United States Patent [19]
Kelsey

[11] 3,994,172
[45] Nov. 30, 1976

[54] MOLTEN METAL SAMPLER
[75] Inventor: Edward A. Kelsey, Disley, England
[73] Assignee: Robert C. Collins, Ashippun, Wis.
[22] Filed: Mar. 14, 1975
[21] Appl. No.: 558,252

[30] Foreign Application Priority Data
  Mar. 20, 1974  United Kingdom............... 12362/74

[52] U.S. Cl. .................... 73/425.4 R; 73/DIG. 9; 249/DIG. 4
[51] Int. Cl.² ........................................ G01N 1/12
[58] Field of Search ............... 73/DIG. 9, 425.4 R; 164/4, 111; 249/DIG. 4

[56] References Cited
UNITED STATES PATENTS
3,321,978  5/1967  Jackson ...................... 73/DIG. 9
3,646,816  3/1972  Hance et al. .................. 73/DIG. 9

FOREIGN PATENTS OR APPLICATIONS
1,526,144  4/1968  France ......................... 73/DIG. 9

*Primary Examiner*—S. Clement Swisher
*Attorney, Agent, or Firm*—Cyril M. Hajewski

[57] ABSTRACT

A receptacle for extracting a sample of molten metal from a furnace while the metal is in the furnace or is being poured from it. The receptacle is formed of a mineral fiber or other suitable material having high heat insulating qualities with a portion of the wall of the receptacle being formed of a material that is a relatively good conductor of heat. The proportion of insulating material to good heat conducting material is such as to obtain the desired control of the solidification of the metal by preventing premature chilling and thereby improving the quality of the sample. The good heat conductor preferably presents a smooth surface to obtain a corresponding smooth surface on the metal sample to facilitate processing it in the metallurgical laboratory.

10 Claims, 19 Drawing Figures

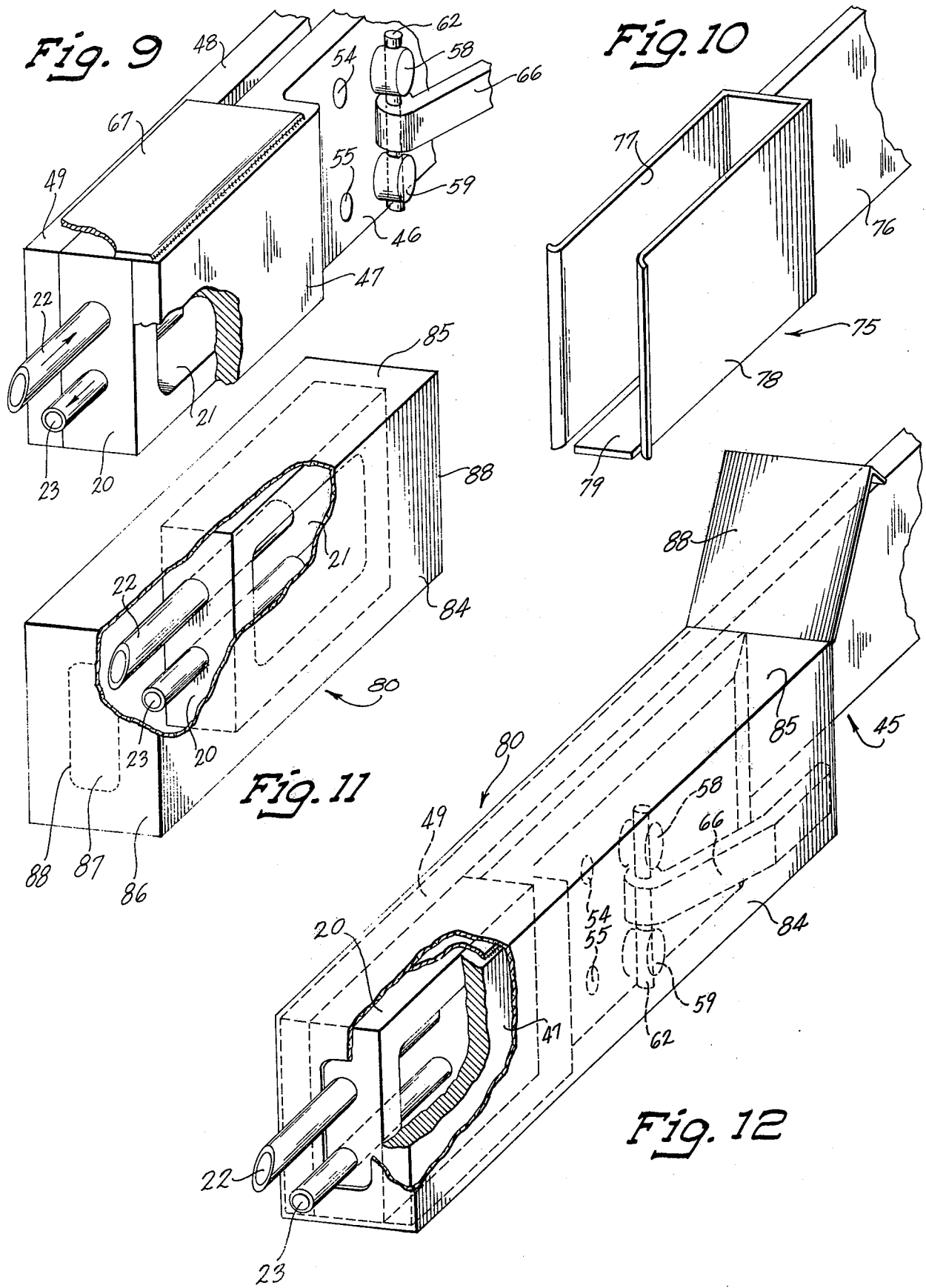

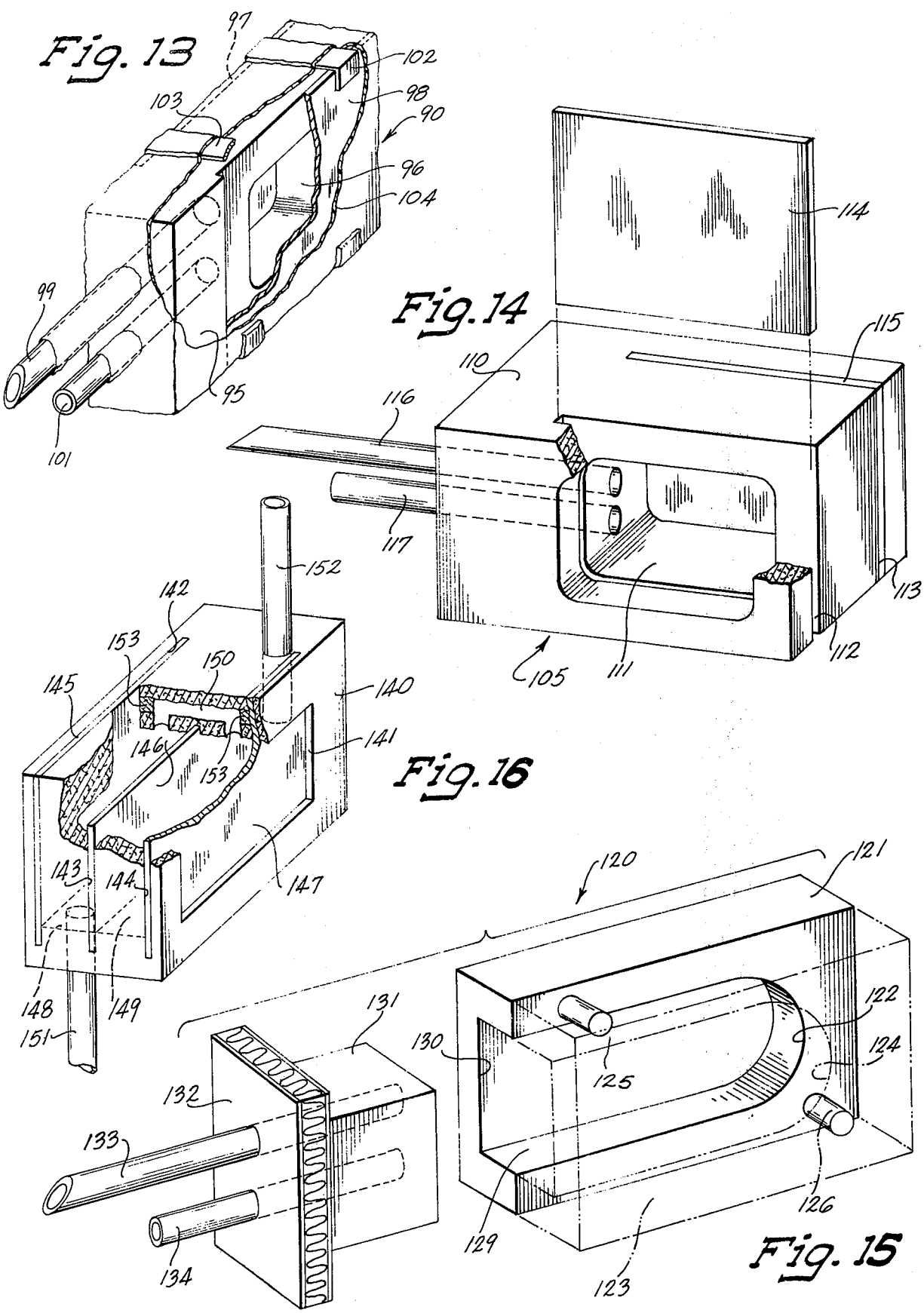

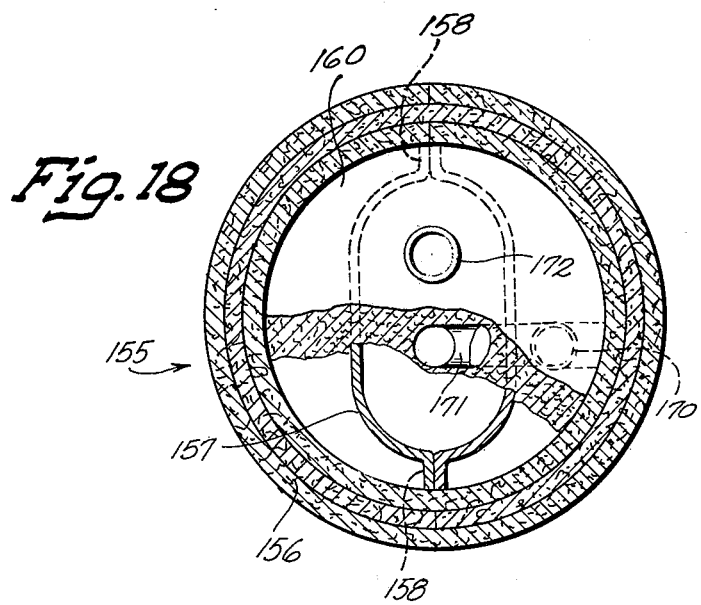
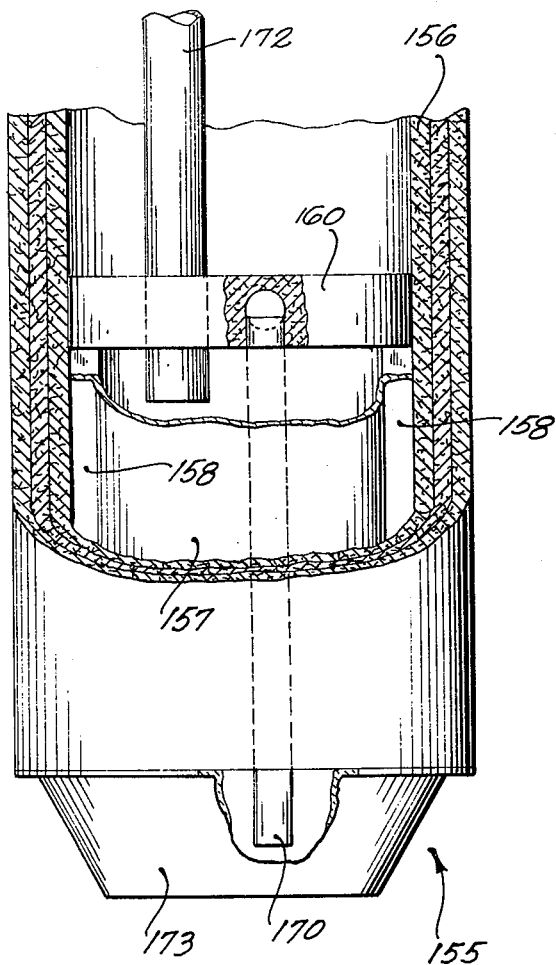
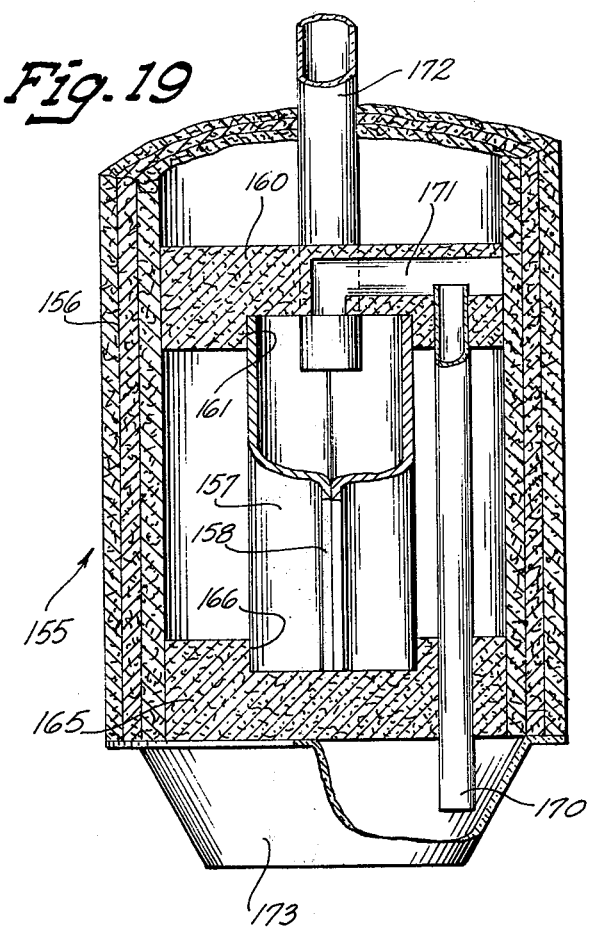

MOLTEN METAL SAMPLER

BACKGROUND OF THE INVENTION

In the metallurgical field it is necessary to obtain samples of the metal while it is in the molten state for various analyses to determine the composition and quality of the metal being processed. It is essential that the sample be a good representation of the metal in the furnace and that the sample be a good solid specimen free of extraneous material of any kind. It also is desirable to obtain a sample in a round flat form especially adapted for polishing and in the form of a pin that can be readily processed in the laboratory for metallurgical analyses.

It has been the conventional practice in the past to utilize a metal receptacle for receiving the molten metal to form the specimens for laboratory analyses. The receptacle with the specimen is broken open and disposed of. However, the use of a metal receptacle usually resulted in excessively rapid chilling and solidification of the specimen which will result in undesirable voids in the sample because the metal is not allowed to circulate sufficiently in the mold to vent all of the gases.

Moreover, the solidified metal sample adheres to the metal receptacle and it is difficult to break open the receptacle for gaining access to the sample.

When taking such sample of metal from a furnace it is imperative that the rate of cooling of the sample be controlled to prevent its rapid chilling and premature solidification. Such excessively rapid cooling produces a poor sample that is not entirely satisfactory for laboratory purposes. Thus, for example, it may cause stratification in the sample making it unsuitable for metallurgical analyses. Furthermore, such rapid cooling may trap gases in the metal which will produce undesirable voids in the sample.

SUMMARY OF THE INVENTION

The invention comprises an improved receptacle for receiving samples of molten metal from a producing furnace or the like to form metal specimens which are used by the laboratory in making metallurgical analyses to determine the quality of the entire melt in the furnace. The receptacle is conveniently formed of two different materials, each of which has different heat conducting qualities. Thus, a mineral fiber, such as ceramic fiber is used to form a portion of the walls of the receptacle while a good conducting material such as metal is employed for forming the other walls. The mineral fiber inhibits the conductance of the heat away from the molten metal in the receptacle and therefore delays its solidification. The more wall area that is formed of the mineral fiber material, the greater the delay in conducting the heat away from the molten metal so that its role of solidification can be controlled by the design of the receptacle which can be adapted to suit any set of conditions.

On the other hand, the walls of the receptacle that are formed of a good conducting material permit some of the heat to be conducted away from the molten metal so that its solidification is not unduly delayed. By forming the receptacle of the correct proportion of good heat conducting material and good heat insulating material, the optimum rate of solidification is obtained for all conditions that may be encountered.

It is therefore a general object of the invention to provide an improved receptacle for receiving molten metal from a furnace or the like to form specimens for laboratory analyses.

It is another object of the invention to provide a molten metal receptacle that produces improved specimens for laboratory analyses but which is inexpensive to manufacture so that it can be disposed of after a single use.

Another object of the invention is to provide a molten metal sampler that can be easily broken apart to gain access to the metal sample contained within it.

A further object of the invention is to provide a molten metal receptacle which controls the dissipation of heat from the molten metal so that its solidification takes place at an optimum rate which will produce the highest grade specimens for laboratory analyses.

A further object of the invention is to provide a molten metal receptacle which can be conveniently employed for taking a sample from a furnace or the like and facilitates the preparation of the produced specimen for laboratory analyses.

The foregoing and other objects of this invention which will become more fully apparent from the following detailed description, may be achieved by means of the exemplifying apparatus depicted in and set forth in this specification in connection with the accompanying drawings.

BRIEF DESCRIPTION OF THE DRAWING

FIG. 9 is a perspective view depicting the molten metal sampler shown in FIG. 1 in position within the jaws of the clamp pictured in FIGS. 5 to 8;

FIG. 10 is a fragmentary perspective view showing the gripping end of an alternate embodiment of the clamp illustrated in FIGS. 5 to 8;

FIG. 11 is a perspective view of a cardboard shipping container enclosing the molten metal sampler shown in FIG. 1 to protect it during shipment as well as during its use;

FIG. 12 is a perspective view showing the cardboard shipping container depicted in FIG. 11 opened sufficiently to render the molten metal sampler operative for receiving a sample of molten metal but still protecting it and its associated clamp while the sample is being taken from the stream of flowing molten metal;

FIG. 13 is a perspective view of another embodiment of the present invention with a portion broken away to illustrate the interior structure;

FIG. 14 is a perspective view of another embodiment of the present invention with a portion broken away to better illustrate the structure;

FIG. 15 is a perspective exploded view of another embodiment of the present invention;

FIG. 16 is a perspective view of another embodiment of the present invention which is especially adapted to be immersed in the molten metal to take the sample, parts of the structure being broken away to show the interior structure;

FIG. 17 is a fragmentary view in front elevation showing another embodiment of the present invention which is especially adapted fo being immersed in the molten metal to take the sample, parts of the view being broken away to depict the interior structure;

FIG. 18 is a view in horizontal section through the molten metal sampler illustrated in FIG. 17; and FIG. 19 is a fragmentary view in side elevation of the molten metal sampler shown in FIG. 17 with parts broken away to illustrate the interior structure.

DESCRIPTION OF THE PREFERRED EMBODIMENTS

Figure 1:
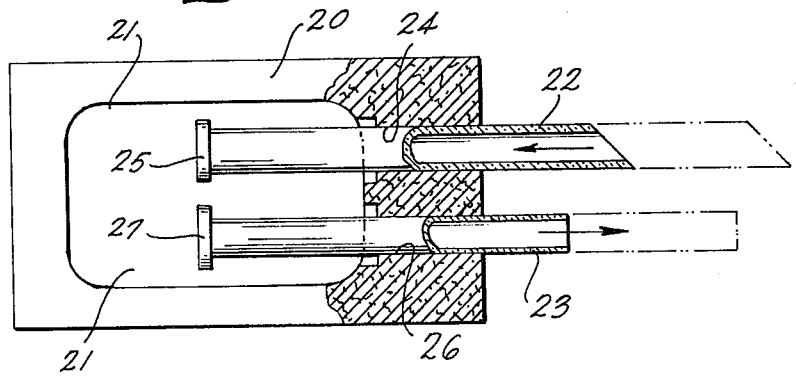
FIG. 1 is a view in front elevation illustrating a molten metal sampler incorporating the features of the present invention and especially adapted for taking a sample of molten metal as it is flowing out of a receptacle.
Figure 2:
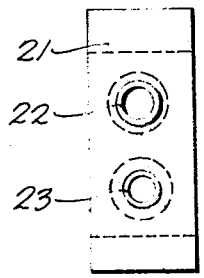
FIG. 2 is a view in side elevation of the molten metal sampler shown in FIG. 1.

Reference is now made more particularly to the drawings and specifically to FIGS. 1 and 2 thereof which illustrate an embodiment of a molten metal sampler body that is adapted to cooperate with a metal clamp for taking a sample of molten metal out of a stream as the metal is flowing from one receptacle to another. Since the molten metal sampler shown in FIGS. 1 and 2 is especially adapted to take a sample of molten metal as the metal is flowing, the sampler is known in the art as a stream sampler. The illustrated embodiment comprises a body 20 formed of a relatively soft insulating material that will withstand the heat of molten metal. It has been found that a mineral fiber such as ceramic fiber is ideally suited for forming the body 20. Such material is extremely easy to form by simply cutting it to the desired shape, and it provides the heat withstanding qualities as well as the insulating qualities necessary to regulate the cooling of the molten metal sample that is taken from the stream to vastly improve the quality of the sample taken for test purposes.

The body 20 is provided with a central aperture 21 that cooperates with the jaws of a clamp, to be later described, for forming a chamber that receives the molten metal. The body includes a filler tube 22 and a sample tube 23 which are formed of a heat resistant material such as ceramic or quartz. The filler tube 22 extends through a bore 24 in the body 20 into the aperture 21 and the end within the aperture 21 is provided with a flange 25 that is cemented thereto for preventing the withdrawal of the tube 22 from the aperture 21. In like manner the tube 23 extends through a bore 26 into the aperture 21 and the end within the aperture is provided with a flange 27 that likewise prevents its withdrawal therefrom.

The tubes 22 and 23 are slidable within the bores 24 and 26 so that they may be slid as far as possible into the aperture 21 to reduce the size of the body 20 for shipping purposes. However, when the assembly is to be put to use the tubes 22 and 23 are withdrawn from the aperture 21 until their respective flanges 25 and 27 bear against the body 20. The tubes 22 and 23 will then be in the position shown by the broken lines in FIG. 1.

The tube 22 is the filler tube for admitting the molten metal into the chamber formed by the aperture 21 and after the chamber is filled the molten metal will continue to flow into the sample tube 23 to form a pin. Thus, two types of samples are formed by the sampler. The chamber formed by the aperture 21 will form a block that may be polished for metallurgical analysis and the tube 23 will form a pin that is especially adapted for manipulation to conduct other types of analyses.

Figure 3:
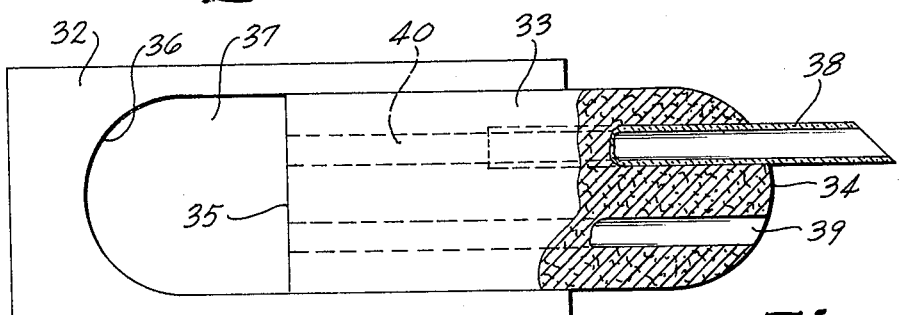
FIG. 3 is a view in front elevation showing an alternate embodiment of the invention depicted in FIG. 1.
Figure 4:
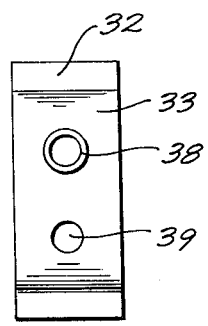
FIG. 4 is a view in side elevation showing the embodiment illustrated in FIG. 3.

The embodiment illustrated in FIG. 3 is an adaptation of the body shown in FIG. 1 and comprises a body 32 which is also formed of a relatively soft insulating material such as a mineral fiber in the same manner as the body 20 of FIG. 1. However, instead of an aperture being cut out of the central portion of the body a U-shaped member 33 is cut out of the entire body as shown and then reversed so that its rounded end 34 extends outwardly of the body 32 and its flat end 35 cooperates with the rounded end 36 of the cutout to form an aperture 37 for receiving the molten metal. The U-shaped cutout 33 includes a filler tube 38 for admitting the molten metal into the chamber 37 and a bore 39 is formed in the cutout 33 for receiving molten metal to form a sample pin for metallurgical analyses.

The tube 38 is formed of quartz or ceramic and extends partway into a bore 40 formed in the cutout 33. This tube is preferably cemented in position. The molten metal flows into the tube 38 to the chamber 37 and then the molten metal flows into the bore 39 to form the sample pin.

Figure 5:
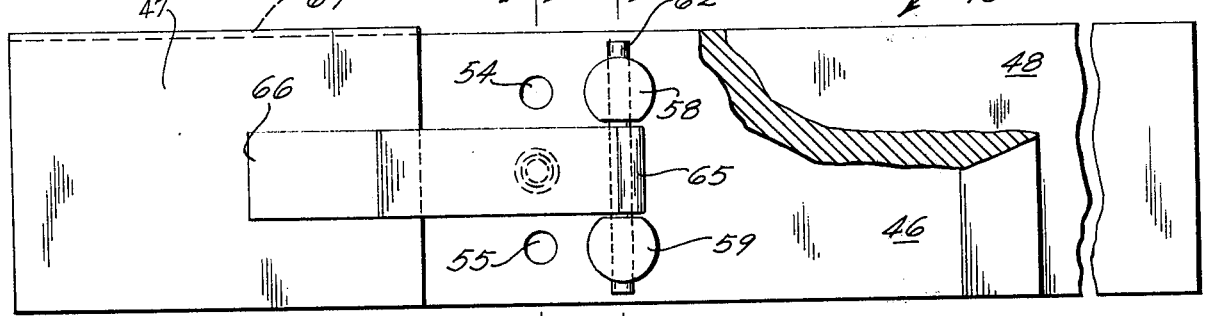
FIG. 5 is a view in front elevation depicting a metal clamp for holding the molten metal samplers illustrated in FIGS. 1 and 3 as they are inserted in a stream of molten metal for receiving a sample of the metal.
Figure 6:
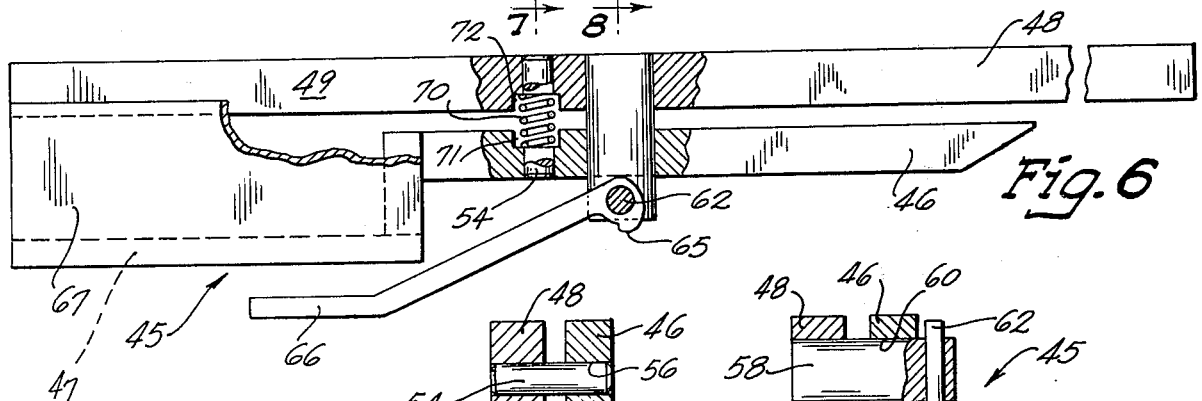
FIG. 6 is a plan view of the clamp shown in FIG. 5 with a portion broken away to reveal a spring for forcing two portions of the clamp apart.

The bodies illustrated in FIGS. 1 to 4 are adapted to cooperate with a metal clamp for forming the metal sample from the molten metal. One type of metal clamp that will function with these bodies is illustrated in FIGS. 5 to 8 and is generally identified by the reference numeral 45. The clamp 45 comprises a top plate 46 having a jaw 47 and a bottom plate 48 having a jaw 49. A pair of dowels 54 and 55 are secured to the bottom plate 48 and extend into holes 56 and 57 respectively formed in the top plate 46. The dowels 54 and 55 slide within these holes 56 and 57 so that they serve as guides for guiding the movement of the plates 46 and 48 relative to each other. In similar manner two posts 58 and 59 are secured to the bottom plate 48 and extend into bores 60 and 61 formed in the top plate 46. The posts extend beyond the top surface of the top plate 46 for receiving a shaft 62 and a cam 65 is journalled on the shaft 62 between the two posts 58 and 59. The cam 65 is provided with a handle 66 as shown in FIGS. 5 and 6. A plate 67 is welded to the jaw 47 and extends downwardly toward the jaw 49. This plate 67 is provided for the purpose of facilitating the positioning of the block of mineral fiber between the two jaws 47 and 49.

Figure 7:
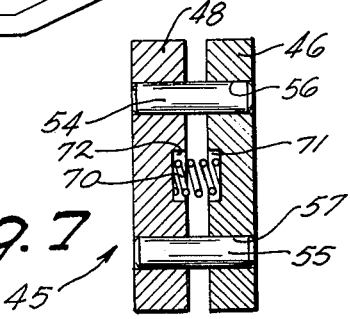
FIG. 7 is a view in vertical section taken along the plane represented by the line 7—7 in FIG. 5.
Figure 8:
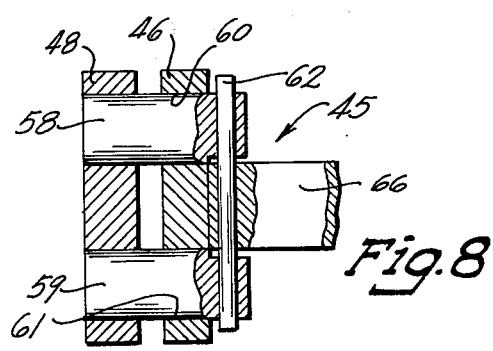
FIG. 8 is a view in vertical section taken along the plane represented by the line 8—8 in FIG. 5.

A spring 70 is centrally disposed between the two plates 46 and 48 to continuously urge the two plates apart and thereby open their jaws 47 and 49 a maximum distance apart. As shown in FIG. 7, one end of the spring 70 is seated in a recess 71 formed in the top plate 46 while the other end of the spring 70 bears against the plate 48 and is located in a recess 72 formed therein.

The clamp is shown in FIG. 6 with the cam 65 released so that the spring 70 has the plates 46 and 48 spread a maximum distance apart causing their respective jaws 47 and 49 to likewise move a maximum distance apart. The body shown in FIG. 1 or the body shown in FIG. 3 is placed between the two jaws 47 and 49 and if one edge of the bodies bears against the plate 67 the bodies will be accurately positioned between the two jaws to insure that the jaws completely cover the apertures 21 or 37. With the bodies thus positioned, the handle 65 is turned in a counterclockwise direction as viewed in FIG. 6, to cause the cam 65 to bear against the flat surface of the top plate 46 and thereby force the plate toward the bottom plate 48 against the pressure of the spring 70 so that the body 20 or the body 32 is clamped between the jaws 47 and 49. The clamp 45 with the body 20 or 32 between the jaws 47 and 49 is then attached to a suitable rod (not shown) to place the entire assembly in position in the stream of molten metal for receiving the molten metal. Assuming, for example, that the embodiment shown in FIG. 1 is placed between the jaws 47 and 49, the aperture 21 is closed by the two jaws 47 and 49 of the clamp 45 to form a chamber for receiving the molten metal.

Since a portion of the chamber walls are formed of the insulating material 20 and a portion are formed of the metal of the jaws 47 and 49 the cooling of the molten metal in the chamber will be slowed due to the insulating qualities of the body 20 and yet the metal jaws 47 and 49 will permit cooling at a sufficiently rapid rate so as not to unduly hinder the process. Moreover, the smooth metal jaws 47 and 49 will furnish a smooth surface to facilitate polishing and the tube 23 will provide a sample pin for metallurgical analyses.

After the sample has cooled within the chamber, the handle 66 of the clamp 45 is moved in a clockwise direction as illustrated in FIG. 6 to release the cam 65 and permit the plates 46 and 48 to separate. This separates the jaws 47 and 49 so that the body 20 and the molten metal samples contained therein can be removed. The body 20 is then broken apart to remove the sample and the clamp 45 is reused with another body 20 for taking another sample.

The type of clamp that is employed for holding the body 20 may vary. It is only important that it provide two metal jaws that bear against the body 20 for closing the aperture 21 to form the chamber for receiving the molten metal and the jaws must hold the body 20 tight enough to hold it while the sampler is in the stream of molten metal. Another type of clamp is illustrated in FIG. 10 and is generally identified by the reference numeral 75. It is a simpler unit having a handle 76 and two spring jaws 77 and 78. A plate 79 extends longitudinally from the handle 76 to provide a bearing surface for receiving the body 20. The body 20 is inserted between the two spring jaws 77 and 78 and their spring characteristics hold the body 20 between them when receiving the molten metal. The jaws 77 and 78 also function as do the jaws 47 and 49 of the clamp 45 for closing the aperture 21 to form the chamber for receiving the molten metal.

When inserting the fiber body and its associated clamp in the stream of molten metal it is desirable to protect the entire assembly by a suitable heat resistant material such as paper board. To this end, FIGS. 11 and 12 show a paperboard carton that is especially adapted for shipping the body 20 with its tubes 22 and 23 to protect the unit during shipment and which can also remain on the body 20 and its associated clamp while the molten metal is being received to protect the unit from the high temperatures encountered. To this end, the cardboard protective covering 80 is in the form of a closed box to enclose the body 20 and its tubes 22 and 23 while the unit is being shipped. It includes a pair of parallel side walls 84 connected by parallel top and bottom walls 85 which are united with the side walls 84 to form a rectangular enclosure. One end of this enclosure is closed by an end wall 86 that has a removable tab 87 which is attached to the end wall 86 by a perforated line 88 so that it can be readily removed. The opposite end of the enclosure 80 is closed by a flap 88 so that the side walls 84, the top and bottom walls 85, the end wall 86 and the flap 88 all form a closed box for enclosing the body 20 with its tubes 22 and 23.

The body 20 is centrally located in the cardboard box 80 and is held in such position by suitable wire staples (not shown) in well known manner. When the unit is to be placed into operation the jaws of the clamp 45 are moved into the box 80 with one jaw on each side of the body 20. The clamp jaws are forced forwardly to rupture the wire staples (not shown) and the forward movement of the body 20 causes the tubes 22 and 23 to break the tab 87 from the wall 86 so that they can pass through the opening and extend out of the box 80 as shown in FIG. 12. With the clamp 45 and the body 20 thus protected by the cardboard enclosure 80, the unit is placed in the stream of molten metal for receiving the sample that is to be employed for metallurgical analyses. Thus, the enclosure 80 serves as a container for the body 20 and its tubes 22 and 23 during shipment of the assembly and it also serves to protect the unit when the sample is being taken from the stream of molten metal.

The previously described embodiments were especially adapted for employment with metal clamps such as the clamps 45 and 75. However, the invention may be practised without the use of such clamps by merely providing a metal plate to close the aperture in the mineral fiber body. Such embodiments are illustrated in FIGS. 13 and 14. The unit shown in FIG. 13 is identified generally by the reference numeral 90 and comprises a mineral fiber such as ceramic fiber body 95 having an aperture 96 formed therein. The aperture 96 is illustrated as being of rectangular configuration with rounded corners but it is to be understood that this may be formed in the fiber body 95 as circular or any other configuration that may be desired and of any size within the limits of the size of the body 95. The aperture 96 is closed on one side by a plate 97 and on the opposite side by the plate 98 so that the aperture 96 with the plates 97 and 98 form a chamber which is accessible through a filler tube 99. The tube 99 is formed of quartz or other heat resistant material and extends through a suitable drilled hole in the body 95 so that it is in communication with the aperture 96. A similar tube 101 extends through a drilled hole in the body 95 into communication with the aperture 96 so that the molten metal 96 will flow into the tube 101 to form a pin as a sample for metallurgical analyses. The two plates 97 and 98 are located in recessed portions of the body 95 and are held in position by a pair of clips 102 and 103.

The molten metal sampler 90 shown in FIG. 13 is a complete unit that is merely attached to a suitable long handle so that it can be inserted into a stream of molten metal for receiving the sample. The metal will flow through the filler tube 99 into the chamber formed by the aperture 96 and the two plates 97 and 98 and then into the tube 101 to form the sample pin. With this arrangement, the rate of cooling of the molten metal in the chamber will be controlled by a suitable proportion of fibrous insulating material and metal plates forming the walls of the receiving chamber. Moreover, the two metal plates 97 and 98 will form smooth flat surfaces on the metal sample which facilitates polishing and otherwise preparing the sample for tests.

The molten metal sampler 90 depicted in FIG. 13 is shown as having a protective coating 104 which may be desirable when the sampler is subjected to rough use and extremely high temperatures. Such coating will add physical strength to the assembly and will also protect it against the extremely high temperatures that may be encountered. A suitable coating for this purpose is a ceramic cement. However, it has been found that a more efficient material which is more economical is a suitable ablative material such as Dow Corning No. 93-104 ablative material. Such ablative material will add to the strength of the sampler when it is put into operation and will also provide temporary protection from the extremely high heat of the molten metal. However, after being subjected to the heat for a short period of time the ablative material disintegrates and disappears so that it does not interfere with the removal of the metal from the sampler. Thus, the ablative provides the protection desired while the sampler is being used but then disappears so that it does not make it any more difficult to remove the metal sample from the sampler.

The embodiment illustrated in FIG. 14 is similar to that shown in FIG. 13 except that the metal plates are inserted in slots formed in the fibrous body rather than held in position by clips. Thus, the embodiment illustrated in FIG. 14 is generally identified by the reference numeral 105 and comprises a body 110 formed of a mineral fiber and has an aperture 111 formed therein. The body 110 also has a pair of parallel slots 112 and 113 cut into it with the slots extending from one end of the body through the entire aperture 111 and into a portion of the body on the opposite side of the aperture 111. The slot 112 receives a metal plate 114 which is shown above the slot disassembled from the body 110 while the slot 113 receives a plate 115 which is shown assembled to the body 110 in the slot 113.

It is to be understood that when the unit 105 is placed in operation, the plate 114 will be inserted into the slot 112 to form a closed chamber with the plate 115 and the aperture 111 for receiving the molten metal that is to be sampled. A filler tube 116 extends through a hole drilled in the body 110 into communication with the chamber 111 and a sample tube 117 likewise extends through a drilled hole in the body 110 into communication with the chamber 111. As in previously described embodiments, the molten metal flows through the filler tube 116 into the chamber formed by the aperture 111 and the plates 114 and 115 and then from the chamber the metal flows into the tube 117 to form a sample pin.

In the previous embodiments the body portion of the assembly is formed of an insulating material such as a mineral fiber and has an aperture which is closed by metal plates. The fiber body decreases the rate of cooling of the molten metal so that a desired mixture is obtained but in some cases it may be desired to accelerate the cooling somewhat while still preventing the rapid cooling of an entire metal molten sampler unit. To this end, the embodiment illustrated in FIG. 15 provides a metal body generally identified by the reference numeral 120. The body 120 comprises a rectangular metal half 121 having a U shaped recess 122 which cooperates with an identical unit that is illustrated by broken lines in FIG. 15. Accordingly, the other half of the unit comprises a metal body 123 having a U shaped recess 124. Thus one half of the body 120 is formed by the portion 121 and the other half is formed by the portion 123 that is shown by broken lines in FIG. 15. The two body portions 121 and 123 are aligned and held together by a pair of dowels 125 and 126. The two U shaped recesses 122 and 124 also cooperate to form one metal walled chamber 129 that has a rectangular opening 130.

In order to reduce the rate of cooling in the chamber 129 to some extent, the rectangular opening 130 is closed by a rectangular block 131 formed of heat insulating material such as a mineral fiber. A corrugated cardboard plate 132 is attached to the exterior surface of the closure block 131 to protect the unit from the molten metal as the sampler is placed in the stream of flowing metal. A filler tube 133 extends through the cardboard plate 132 and the closure block 131 to have communication with the chamber 129 so that the molten metal will flow through the tube 133 into the chamber 129. Molten metal in the chamber 129 will also flow into a sample tube 134 which is provided for forming a sample pin that will be tested in a metallurgical laboratory. Thus, the closure block 131 formed of insulating material will reduce the rate of cooling of a molten metal in the chamber 129 but not to the extent that it is reduced in any of the previously described embodiments. However, as in the previous embodiments, a portion of the molten metal sampler is formed of metal and another portion is formed of an insulating material so that the cooling rate of the metal in the receiving chamber is controlled. Since the body portions 121 and 123 are made of metal they are intended to be reused and only the block 131 and plate 132 with their tubes 133 and 134 will be disposed of after a single use.

The previously described embodiments of the molten metal sampler are especially adapted to take a sample of metal as it is flowing from one receptacle to another and are therefore referred to as stream samplers. However, it is also frequently necessary to take a sample of molten metal while it is in a furnace or other receptacle and this is done by immersing the sampler into the molten metal to receive the sample. Such samplers are known as immersion samplers. An immersion sampler constructed in accordance with the teachings of the present invention is illustrated in FIG. 16. As there shown, the sampler comprises a body 140 which is formed of insulating material such as a mineral fiber in the same manner as the bodies of the previous embodiments were formed. A rectangular aperture 141 is formed in the body 140 and three parallel slots 142, 143 and 144 are formed in the body 140 to extend from one end thereof through the entire aperture 141 and into the body 140 a slight distance beyond the aperture 141. The central slot 143 does not extend through the entire height of the body 141 as do the slots 142 and 144. A metal plate 145 is inserted into the slot 142 and another metal plate 146 of lesser height is inserted into the slot 143. A metal plate 147 identical to the plate 145 is inserted in the slot 144. These three metal plates form two chambers 148 and 149 in the body 140 but communication between the two chambers 148 and 149 is provided by a U-shaped passage in the body 140 above the center plate 146 and the chamber 148 and 149.

The passage 150 is formed by a long horizontal bore and two short vertical legs in communication with it. The horizontal bore can be formed by drilling a hole completely through the body 140 and closing its ends with plugs 153. A filler tube 151 extends downwardly from the body 140 and is in communication with the chamber 148. A sample tube 152 extends upwardly from the body 140 and is in communication with the chamber 149.

In operation, the unit illustrated in FIG. 16 is filled through the filler tube 151 which admits the molten metal into the chamber 148. This chamber serves as a mixing chamber and may also contain a deoxydent for removing the oxygen from the metal. When the chamber 148 is full it flows through the passage 150 into the chamber 149 and also fills the sample tube 152 to form a sample pin for metallurgical testing. As previously mentioned, the unit is an immersion unit so that it is immersed in the molten metal. When it is withdrawn from the molten metal, the metal may flow out of the chamber 148 through the tube 151 but the metal in the chamber 149 and the pin 152 is trapped therein and cannot escape so the metal in the chamber 149 and the pin 152 is the sample of metal that will be subjected to metallurgical analyses. However, it should be still noted that a portion of the chamber 149 is formed by walls of insulating material while other walls of the chamber are formed of metal so that the cooling rate of the sample is accurately controlled.

FIGS. 17 to 19 inclusive illustrate another embodiment of an immersion type molten metal sampler which is generally identified in the drawings by the reference numeral 155. The sampler comprises a cylinder 156 formed of paperboard or other material which will protect the sampler when it is immersed in the molten metal. Pressed into the interior bore of the cylinder 156 is a metal receptacle 157 that has flanges 158 which are pressed against the paperboard cylinder 156 to help retain the receptacle 157 in the cylinder 156. The top of the receptacle 157 is closed by a circular mineral fiber cap 160 which fits into the bore of the cylinder 156 and is secured in place for closing the top of the receptacle 157. As illustrated in FIG. 19, a recess 161 is formed in the bottom face of the cap 160 for receiving the top edge of the receptacle 157. The recess 161 serves to provide a good seal between the cap 160 and the receptacle 157 and also assists in supporting the latter within the cardboard cylinder 156.

A similar circular base 165 formed of a mineral fiber to provide good insulating qualities is secured in the bottom of the cylinder 156 for closing the bottom opening of the receptacle 157. The base 165 is provided with a recess 166 for receiving the lower edge of the receptacle 157. Thus, the receptacle 157 is supported at its top by the cap 160 and at its bottom by the base 165. The receptacle 157 is formed of metal but the cap 160 and the base 165 are formed of an insulating material such as a mineral fiber. The combination is such that the cooling of the sample formed within the receptacle 157 is controlled to yield a metal sample of optimum qualities.

A filler tube 170 is formed of quartz or other heat resistant material and extends beneath the lower face of the base 165. The tube 170 extends upwardly through the base 165 and through a portion of the cap 160 to communicate with an L-shaped passageway 171 which has been formed in the cap 161. The long leg of the L-shaped passageway 171 extends horizontally as shown in FIG. 19 and the short leg extends 90° therefrom into the bottom face of the base 160 to communicate with the interior of the receptacle 157. A sample tube 172 also extends through the cap 160 into communication with the interior of the receptacle 157. The extending bottom end of the filler tube 170 is protected by a circular cover 173 which is formed of a heat sensitive material that will disintegrate when exposed to heat. The cover 173 will permit the entire unit to pass through the slag on top of the molten metal without admitting any of it into the filler tube 170. After the sampler passes through the slag the heat of the molten metal will cause the cover 173 to disintegrate and pure metal will then be admitted into the sampler.

In operation, when the unit is immersed in the molten metal beneath the slag, the protective cover 173 will disintegrate to render the open bottom end of the filler tube 170 accessible to the metal. The molten metal will flow up the tube 170 through the passage 171 into the interior of the receptacle 157 and then up the sample tube 172. The sampler may then be removed from the molten metal, and because of the fact that the receptacle 157 and pin 172 have been filled by the flow of metal through the passage 171, the molten metal cannot escape when the sampler is removed from the metal. Accordingly, the receptacle 157 and the sample tube 172 will retain the molten metal to form the two types of samples and since the cap 160 and the base 165 are formed of an insulating material, the rate of cooling will be controlled so that the metal samples will solidify at the most desirable rate so that the samples are of optimum quality.

The unit 155 is shown with the filler tube 170 extending downwardly of the unit and in communication with the passage 171 because this facilitates the assembly and manufacture of the protective cover 173. However, the filler tube 170 can be eliminated entirely and the passage 171 extended through the wall of the cylinder 156. With this arrangement the molten metal would flow directly through the passageway 171 into the receptacle 157.

Although a deoxidant is not shown in the drawings, all of the embodiments shown and described are intended to function with a deoxidant to remove gases from the molten metal. Various deoxidants have been used for this purpose, such as aluminum, titanium or zirconium and the deoxidant can be placed in either the filler tube or the chamber that receives the molten metal. Thus a length of aluminum wire extending through the bore of the filler tube would serve the purpose very well. Such deoxidants will function exceptionally well with the present invention because the rate of cooling of the molten metal has been reduced and the deoxidants can therefore operate more efficiently to remove the gas from the molten metal.

All of the illustrated embodiments will be mounted on the end of a long rod (not shown) in well known manner when obtaining the samples of molten metal. Such rod will enable the person taking the sample to safely place the metal sampler in the molten metal without getting too close to the melt.

From the foregoing detailed description of the illustrative embodiments of the invention set forth herein, it will be apparent that there has been provided an improved molten metal sampler which facilitates the taking of metal samples either from a stream of metal flowing from one container to another, or from a contained heat of metal by means of an immersion type sampler. The improved molten metal sampler regulates the rate of cooling of the samples that are obtained to improve their quality and provide uniform good results and although the improved sampler is inexpensive to manufacture it is extremely flexible in the ability to change the form of the samples taken by the improved arrangement.

Although the illustrative embodiments of the invention have been described in considerable detail for the purpose of disclosing practical, operative arrangements by means of which the invention may be practised advantageously, it is to be understood that the particular molten metal samplers illustrated and described are intended to be illustrative only and that the various novel characteristics of the invention may be incorporated in other structural forms without departing from the spirit and scope of the invention as defined in the subjoined claims.

The principals of this invention having now been fully explained in connection with the foregoing description, I hereby claim as my invention:

1. In a molten metal sampler for receiving samples of molten metal that are to be solidified in a particular configuration for metallurgical testing; a body formed of an insulating material and having a hole formed through said body so that the hole is open at both ends; a plate covering each of the two openings of the hole to cooperate with the body for forming a chamber for receiving the molten metal, each of said plates being formed of a good heat conducting material with their exterior surfaces being exposed to the atmosphere when the sampler is removed from the molten metal so that they can continue to conduct heat away from the molten metal in said chamber; securing means for securing said plates in position over the open ends of the hole; and a filler passage formed through said body for admitting the molten metal into said chamber, whereby the rate of cooling of the molten metal sample in the chamber will depend on the proportion of insulating walls to good head conducting walls forming the chamber.

2. A molten metal sampler according to claim 1 wherein said body is formed of ceramic fiber with the hole cut into said fiber; and said plate is made of metal.

3. A molten metal sampler according to claim 1 wherein the exterior surfaces of the assembly are coated with a protective material that will strengthen the assembly so that it will withstand more abuse from handling and from operation in the molten metal and will also protect the assembly from the high heat of the molten metal being sampled.

4. A molten metal sampler according to claim 3 wherein said protective coating is an ablative material that will provide initial insulation and strength to the assembly but will be dissipated from the assembly by the high heat of the molten metal after being in the molten metal for a few seconds so that the ablative material will not interfere with breaking the assembly open to obtain the sample metal after it has cooled.

5. A molten metal sampler according to claim 4 wherein said ablative material is Dow Corning No. 93-104 Ablative Material.

6. A molten metal sampler according to claim 1 wherein said filler passage is formed by a length of heat resisting tubing extending through said body into said chamber and including a sample tube formed of heat resisting material and being in communication with said chamber to receive a portion of the molten metal flowing through said chamber to form a pin shaped sample for metallurgical analyses while said chamber forms a sample presenting a smooth flat face that can be readily polished for other metallurgical analyses.

7. A molten metal sampler according to claim 1 wherein said plates are formed by two jaws of a clamp between said body is held while the sample of molten metal is being taken from the metal melt.

8. A molten metal sampler according to claim 1 wherein said body is frangible so that it can be readily broken apart to gain access to the metal sample after it has hardened.

9. A molten metal sampler according to claim 1 including a clamp for holding said body while the chamber therein is receiving the sample of molten metal, said clamp comprising two jaws that are adapted to retain said body between them, the jaws serving as said plates for closing the two open ends of the aperture for forming said chamber.

10. A molten metal sampler according to claim 1 including a sample tube formed of heat resisting material and being in communication with said chamber so that a portion of the molten metal flows into it for forming a pin to be used in metallurgical analyses; and a clamp for holding said body while the chamber therein is receiving the sample of molten metal, said clamp comprising two jaws that are movable relative to each other between a clamped position for clamping said body between them and a released position for releasing said body, the jaws serving as said plates for closing the two open ends of the aperture for forming said chamber; and means for actuating said jaws between their released and clamped positions.

* * * * *